United States Patent
Patzwald et al.

(10) Patent No.: US 7,012,698 B2
(45) Date of Patent: Mar. 14, 2006

(54) METHOD AND ARRANGEMENT FOR CONTACTLESS DETERMINATION OF GEOMETRIC AND OPTICAL CHARACTERISTICS

(75) Inventors: Matthias Patzwald, Merbelsrod (DE); Rudolf Kessler, Reutlingen (DE); Waltraud Kessler, Reutlingen (DE); Angela Schindler, Marbach a. Neckar (DE)

(73) Assignee: Carl Zeiss Jena GmbH, Jena (DE)

( * ) Notice: Subject to any disclaimer, the term of this patent is extended or adjusted under 35 U.S.C. 154(b) by 453 days.

(21) Appl. No.: 10/146,452

(22) Filed: May 14, 2002

(65) Prior Publication Data

US 2002/0191192 A1    Dec. 19, 2002

(30) Foreign Application Priority Data

May 15, 2001  (DE) ................................ 101 23 470

(51) Int. Cl.
*G01B 9/02* (2006.01)
(52) U.S. Cl. ...................................................... 356/504
(58) Field of Classification Search ................ 356/450, 356/451, 503, 504

See application file for complete search history.

(56) References Cited

U.S. PATENT DOCUMENTS

| | | | |
|---|---|---|---|
| 5,371,596 A | * | 12/1994 | Hattori et al. ............... 356/504 |
| 5,440,141 A | * | 8/1995 | Horie .......................... 356/504 |
| 5,889,592 A | * | 3/1999 | Zawaideh .................... 356/451 |
| 6,034,772 A | * | 3/2000 | Marcus et al. .............. 356/503 |

* cited by examiner

*Primary Examiner*—Samuel A. Turner
(74) *Attorney, Agent, or Firm*—Reed Smith LLP

(57) ABSTRACT

A method is disclosed for contactless determination of product characteristics, particularly in continuous or discontinuous fabrication of layer systems formed of a plurality of layers with different optical characteristics. The measuring apparatus and measurement methods for determining the characteristics of one of the respective layers are predetermined depending on the optical characteristics of this layer and depending on the optical characteristics of layers situated above it in the measuring direction. In a measuring device for this purpose, a plurality of detectors are provided for wavelength regions directly adjoining one another. The detectors and the signal processing device are constructed such that the light coming from the measurement surface with wavelengths of 200 nm to more than 2400 nm is evaluated in its entirety.

13 Claims, 7 Drawing Sheets

METHOD AND ARRANGEMENT FOR CONTACTLESS DETERMINATION OF GEOMETRIC AND OPTICAL CHARACTERISTICS

CROSS-REFERENCE TO RELATED APPLICATIONS

This application claims priority of a German Application No. 101 23 470.8, filed May 15, 2001, the complete disclosures of which is hereby incorporated by reference.

BACKGROUND OF THE INVENTION a) Field of the Invention

The invention is directed to a method for contactless determination of product characteristics, particularly in continuous or discontinuous fabrication of layer systems formed of a plurality of layers with different optical characteristics. The invention is further directed to an arrangement for implementing the method. The method and arrangement can be used in a particularly advantageous manner in connection with control and quality monitoring in the manufacture of the layer systems mentioned above.

b) Description of Related Art and Discovery of Problems Leading to the Present Invention Measuring devices which operate by spectroscopy and by means of which the reflection and transmission of surface portions on products can be detected are known. Optical characteristics of the products and other quality parameters such as dimensional accuracy of selected product zones can be determined from the measurement spectrum.

For this purpose, an optical measuring head is arranged in a known manner in the immediate vicinity of a product to be characterized. Measurement light is directed from a light source in the measuring head onto a selected measurement surface on the product and the light which is reflected, emitted or transmitted by the measurement surface is then fed to a receiver and subsequently evaluated.

Particularly with respect to highly automated production of multilayer systems, it is desirable to measure the layer construction during the arrangement of the layers or, at the least, shortly before each layer is applied in order to obtain current information about the success of the respective manufacturing step or about the quality of the product and so that corrective measures can be initiated immediately in case of deviations.

In order to achieve fast, reproducible results which are capable of delivering factual information, analytic methods are used which are distinguished by a short analysis period, high analysis frequency, high informational content per time unit, robustness for process installation and operation, reliability, automatability, small space requirement, versatility of detection systems.

However, in the production of layer systems such as have been developed in particular for solar technology, the optical measurement methods and arrangements available in the art are not suitable for carrying out reflection measurements and transmission measurements constantly and with sufficient speed over the entire width of an optical spectrum. Measurements for this purpose are currently still very time-consuming and cost-intensive which, above all, slows down the pace of the manufacturing process.

For this reason, the requirements demanded for production quality have increased considerably in recent years. In particular, requirements for consistency of composition, morphology and, above all, layer thickness are high. In multilayer systems, for example, in the semiconductor industry, in the industrial manufacture of anodizing layers or in the production of modern solar cells based on cadmium sulfide, tight tolerances must be maintained during the course of production.

For purposes of quality control, offline processes are still often used in the art, i.e., spot samples are taken and measured in the laboratory close to operations. However, a direct online or inline measurement during running production operation with, as far as possible, simultaneous detection of different current quality parameters would be desirable.

Optical and spectroscopic methods detect the chemical composition through the interaction of light with the surface by selective absorption and also detect morphological variations through the measurement of scattered light. When the phase relationships between waves are also observed through a suitable arrangement, facts about the layer thickness, for instance, can also be deduced from the interference. In principle, optical and spectroscopic methods are particularly suitable as online and inline measurement techniques because they work very quickly and without contact.

The measurement of interference phenomena is established in the art. Ellipsometric systems have been developed which can determine up to five layers simultaneously. However, for this purpose, all layers must be transparent. In addition, the use of this technique as an online method causes considerable difficulties because it functions reliably only with smooth surfaces. Determination of layer thickness by means of measuring spectral interference is still not considered usable online and its use is restricted to layer thicknesses preferably of 1 $\mu$m or more.

With spectral interference, the layers are typically measured in the wavelength range of visible light from 400 nm to over 700 nm. Usually, a transparent layer (e.g., oxide layer) is applied to an opaque layer (e.g., metal). Accordingly, due to the surrounding light, a three-layer system is formed (with three different refractive indices) which can be described very easily by applying the Fresnel formula. Measurements can be carried out in specular arrangements as well as in diffuse arrangements. The layer thickness is calculated by the interference or specific absorption.

OBJECT AND SUMMARY OF THE INVENTION

Proceeding from the prior art, it is the primary object of the invention to further develop a measurement method of the type described in the beginning in such a way that shorter measuring times are possible with at least the same degree of measurement accuracy. A further object of the invention consists in providing an arrangement for implementing a method of this kind.

According to the invention, in a method of the type described in the beginning, the measuring devices and measurement methods for determining the characteristics of a layer of the layer system are predetermined depending on the optical characteristics of this layer and depending on the layer situated above it in the measuring direction.

The method according to the invention essentially comprises measurement in different spectral ranges (from 0.2 $\mu$m to 30 $\mu$m) by means of different geometric arrangements (e.g., diffuse light with Ulbricht sphere, 45R0, 45R45) depending on the characteristics profile of the individual layers. Surprisingly, wavelength ranges can be selected in such a way that a layer appears transparent, while the other layer is highly absorbent or reflecting and, therefore, an "infinite" layer thickness can be simulated and a simple reflection signal can be received and evaluated.

The characteristics of a plurality of layers of the layer system are preferably determined simultaneously, but, in each instance, with the measuring devices and measuring methods that are predetermined depending on the optical characteristics of the individual layers.

The method according to the invention can be used, for example, for a layer system comprising a molybdenum layer, a CIS layer arranged on the latter, and a CdS layer arranged above the CIS layer. For this purpose, the spectral interference is measured in that IR radiation in a wavelength range for which the molybdenum layer is at least partially transparent is directed to the layer system and the layer thickness of the molybdenum layer is determined from the measurement results, the interference maxima and interference minima are measured in that NIR radiation in a wavelength range for which the CIS layer is at least partially transparent, but for which the molybdenum layer is not transparent, is directed to the layer system and the layer thickness of the CIS layer is determined from the measurement results, and the interference maxima and interference minima are measured in that UV or VIS radiation in a wavelength range for which the CdS layer is at least partially transparent, but for which the CIS layer is not transparent, is directed to the layer system and the layer thickness of the CdS layer is determined from the measurement results.

In a further development of this method, the spectral intensity, for example, is measured, in addition, with a specular and a diffuse arrangement and the roughness of the surface of the molybdenum layer is determined from the difference in the results based on the scattering effect.

Further, it is possible to determine the attenuation of the interference and/or the curve of the reflection of the NIR radiation and to obtain information therefrom about the chemical and morphological makeup of the CIS layer.

It also lies within the scope of the invention to determine the absorption of the UV and VIS radiation and to obtain information about the quality of and semiconductor characteristics of the CdS layer from the position and steepness of the absorption edge.

In all of these variants of the invention, it is possible to assign the spectra to the substance definitively without superposition. In this connection, the quantitative characterization of the layer need not be carried out with complicated and/or time-consuming simulation calculations. When measurements are carried out simultaneously with a plurality of different geometries (spectral goniometry), the diffuse proportions of light can also be detected and evaluated by the scattering. For example, they supply information about the roughness of the surface and scattering centers, but also about the type of defects in the layer. Also, the chemical composition of the layer can be detected simultaneously based on the specific absorption (particularly in diffuse light), while the layer thickness can also be detected (from the interference) simultaneously.

Further, measurement results in the UV range are recorded in parallel with this, so that the characteristics of a product which is to be tested are virtually completely defined. All of the information obtained is detected by the signal processing device, and corresponding evaluation signals and correction signals are obtained from this information depending upon the nature of the measuring task.

In discontinuously running processes as well as continuously running processes, any deviations from the reference quantity of a product or product zone that occur are detected and corrected in a corresponding manner by comparing, constantly or sequentially in predetermined time intervals, to a previously calibrated spectral curve stored in the signal processing device. An evaluation can also be carried out by means of chemometric methods or pattern recognition methods.

Further, the object of the invention is met by a measuring device for determining geometric and/or optical characteristics of the different layers in a layer system, comprising at least one illumination device for illuminating a measurement surface on the product, at least one detector for the light coming from the measurement surface, and a signal processing device which communicates with the signal outputs of the detectors. The illumination device has radiation sources whose radiation completely covers the UV, VIS and IR wavelength regions and detectors are provided for wavelength regions that directly adjoin one another.

The detectors and the signal processing device are constructed such that the light coming from the measurement surface with wavelengths of 200 nm to more than 2400 nm is evaluated in its entirety.

A UV-VIS spectral photometer and an NIR spectral photometer are preferably provided as detectors.

Due to this construction, the detectors detect information from the VIS range (the range of visible light), for example, color characteristics, reflection and transmission of the product to be measured, as well as information from all IR regions (including NIR, MIR), for example, information concerning the concentration of material constituents.

The spectral photometers are preferably constructed as diode array spectral photometers. Photometer systems of this type are distinguished by high thermal stability and wavelength stability and accordingly ensure a constant measurement accuracy.

To achieve a compact, space-saving construction of the measuring device, particularly for a continuously running process, the light source, photometers and signal processing device are advantageously integrated in a common measuring head which is positioned over the measurement surface.

Further, in an advantageous construction, an interface is provided at the signal processing device for communicating with an external computer and/or with a display device.

Insofar as is physically possible, light guides which are preferably flexible and which comprise a plurality of light-conducting fibers are used for transmitting the light which proceeds from the different sources and which is directed to the measurement surface and for transmitting the measurement light to the photometers.

In this connection, in particular, the use of a light guide which is branched in a Y-shaped manner makes it possible for the photometers to be arranged directly adjacent to one another and accordingly favors a compact construction and accuracy of measurement results.

The advantage over other arrangements working, for example, with X rays (X-ray analysis), ellipsometry or gamma ray measurement systems consists in short response time, high measurement frequency, automatability, substantially lower costs, ease of use and ease of maintenance. Very thin layers (less than 20 nm to 100 nm) can also be measured online by means of this measurement technology.

Layer thickness measurement and color-reflection measurement can be carried out parallel with the process. Accordingly, in addition to layer thickness and color, detection of surface structures, e.g., chemical structure or roughness, is also possible.

The present invention make it possible to achieve a measurability of the characteristics of layers and layer systems that are transparent for different spectral regions with measurement systems for different spectral regions which satisfy simple laboratory measurement as well as online or inline measurements. This could be applied in coil or strip coating technologies under vacuum or under normal atmospheric conditions, to mention only one example.

While the coating process is running, determined method steps are repeated at defined time intervals. Deviations from the normal previously calibrated spectral curve which occur as a result of manufacturing technique can be readjusted quickly with the arrangement according to the invention.

Accordingly, a prognosis can be made about the continuing course of the process based on each measurement of a specific technological stage. This makes it possible to determine an optimal time for the conclusion of a coating step by inline measurement.

As was already indicated, for purposes of controlling the arrangement it is necessary to carry out a precalibration of the layers in individual technological stages. The results of the calibration are stored and then used for comparing to the determined actual values.

Accordingly, the very high thermal stability and wavelength stability of the MCS500 UV-VIS-NIR-(IR) spectrometer systems, for example, permit an excellent evaluation according to spectral positions and/or spectral characteristics and their displacements or changes, which is important particularly for determining layer thickness, color and other chemical and physical parameters.

The invention is described more fully in the following with reference to an embodiment example.

DESCRIPTION OF THE PREFERRED EMBODIMENTS

Figure 1:
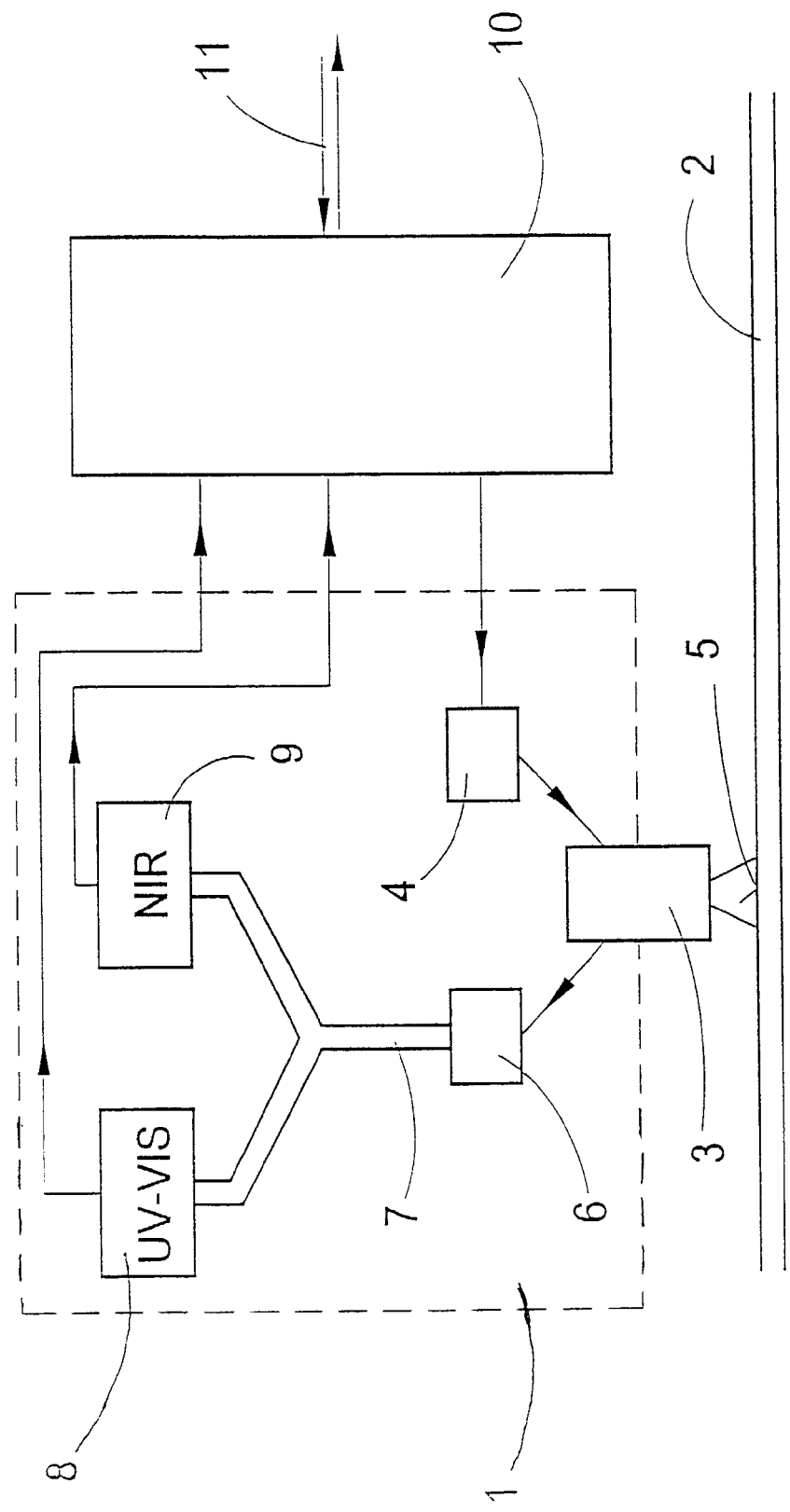
FIG. 1 shows the schematic construction of a measuring device according to the invention.

FIG. 1 shows a simplified view of a measuring device, according to the invention, which is suitable particularly for continuous detection of quality parameters in the coating of a material web, for example, in connection with the production of CIS thin-film modules.

The drawing shows a measuring head 1 which is arranged over a product 2 so as to be adjustable in the x-direction, y-direction and z-direction of a coordinate system. The measuring head 1 has an optical unit 3 which is coupled with an illumination device 4 having radiation sources which completely cover the V, VIS and IR wavelength ranges. The light of the illumination device 4 is directed to a measuring surface 5 on the product 2 by means of the optical unit 3, for example, an objective.

The light that is reflected or emitted from the measurement surface 5 is likewise detected by means of the optical unit 3 and is directed to a detector 6.

A Y-branched light guide 7 through which the measurement light reaches a UV-VIS spectral photometer 8 and an NIR spectral photometer 9 is coupled to the detector 6. The UV-VIS spectral photometer 8 covers the entire ultraviolet range as well as the range of visible light over a total 200 nm to 900 nm, while the NIR spectrometer 9 detects the near infrared range from 900 nm to 2400 nm directly adjacent to the wavelength range of the UV-VIS spectral photometer 8.

The received optical signals are converted to electronic signals in the UV-VIS spectral photometer 8 and in the NIR spectrometer 9 and are forwarded as such to a signal processing device 10. An interface 11 is provided at the signal processing device 10 for purposes of connecting to an external computer and/or a display device.

The detection of the measurement light over the broad wavelength range from 200 nm to more than 2400 nm enables color measurements and layer thickness measurements, for example, of CdS, CIS and ZnO layers.

Figure 2:
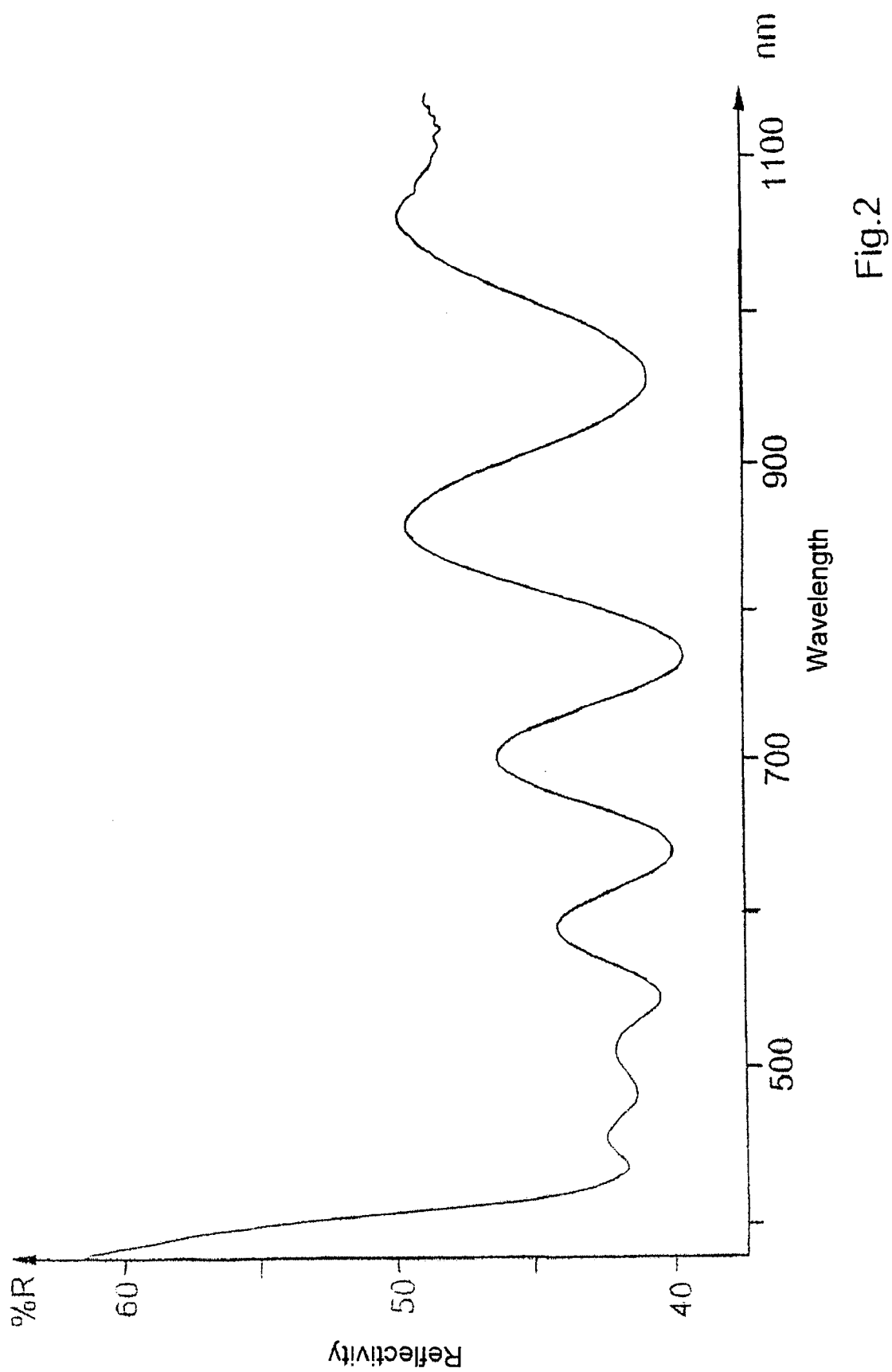
FIG. 2 shows the curve shape of a measurement spectrum.
Figure 3:
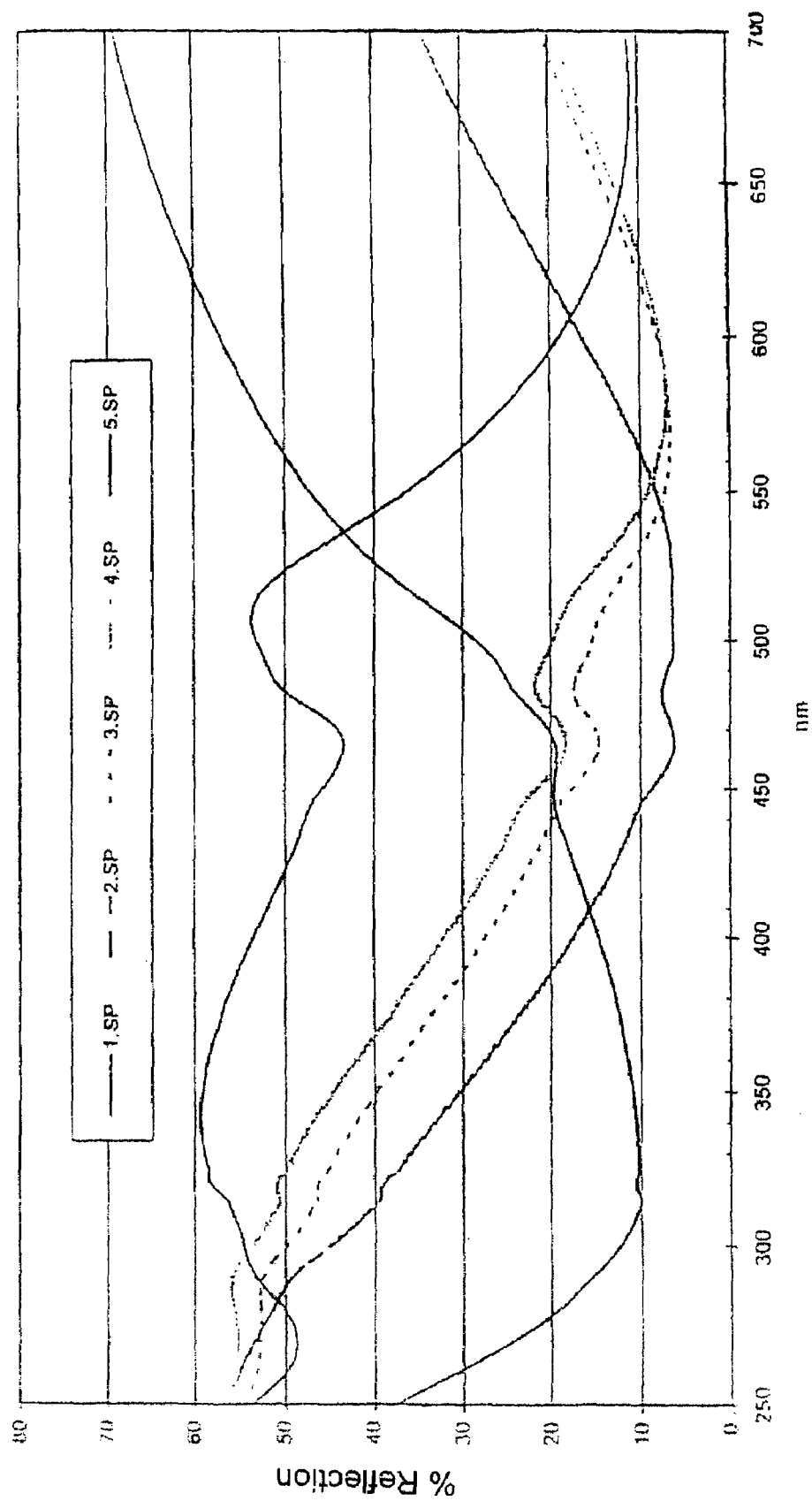
FIG. 3 shows interference spectra of a CdS layer on molybdenum in the UV/VIS wavelength region.
Figure 4:
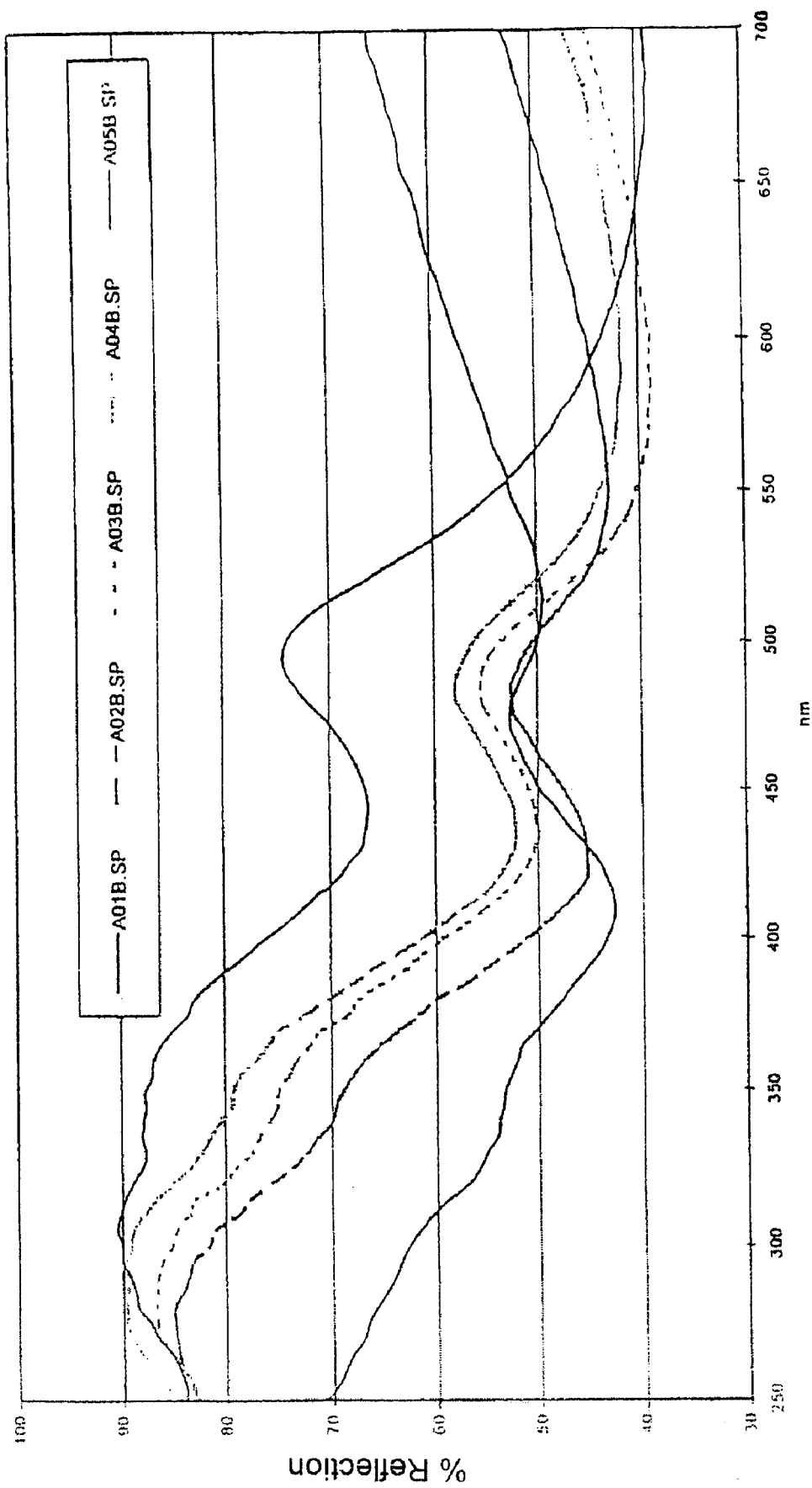
FIG. 4 shows reflection spectra in diffuse reflection of a CdS layer on a CIS layer.
Figure 5:
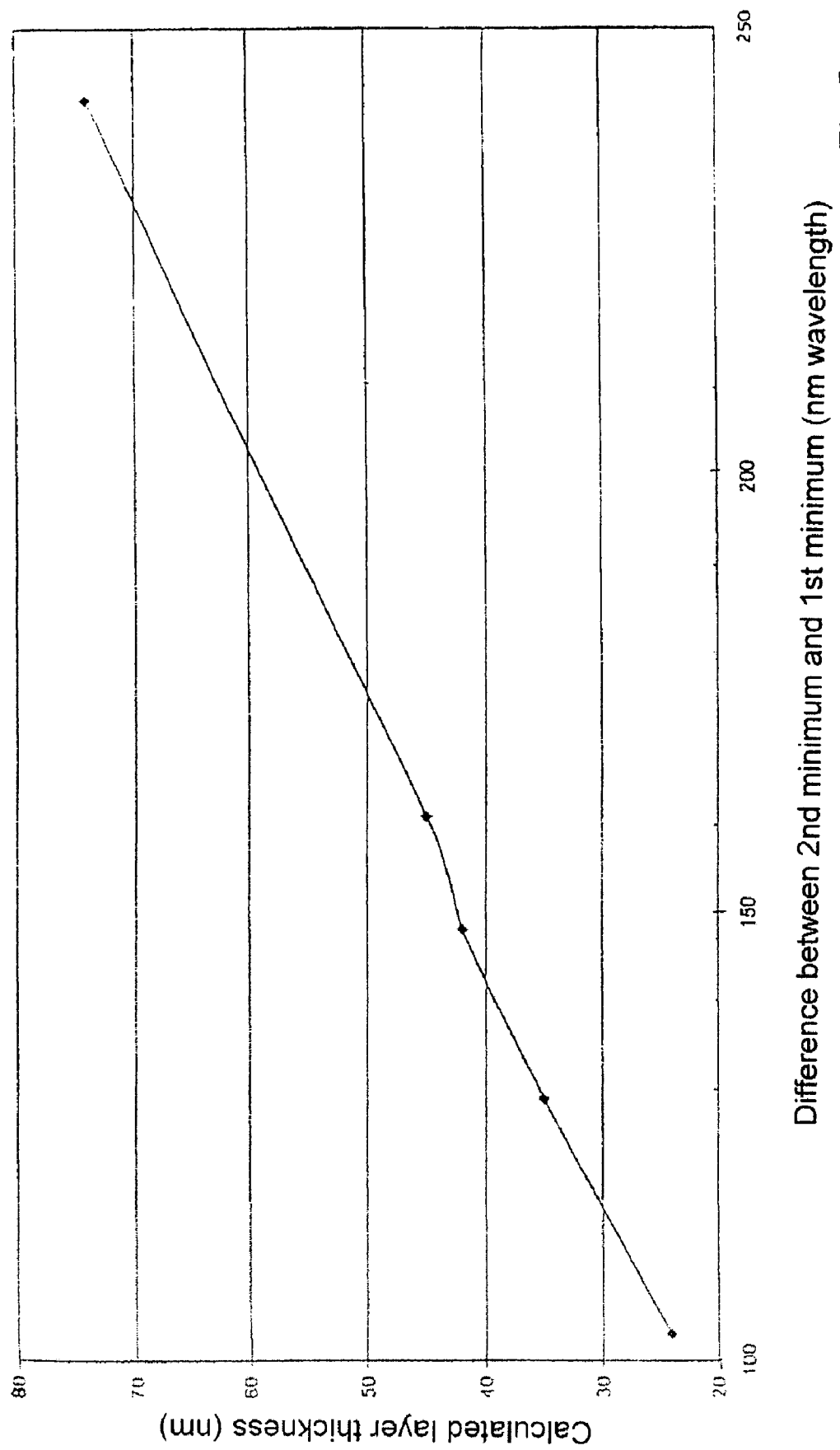
FIG. 5 shows the CdS layer thickness depending on the position of the interference minima with diffuse reflection.
Figure 6:
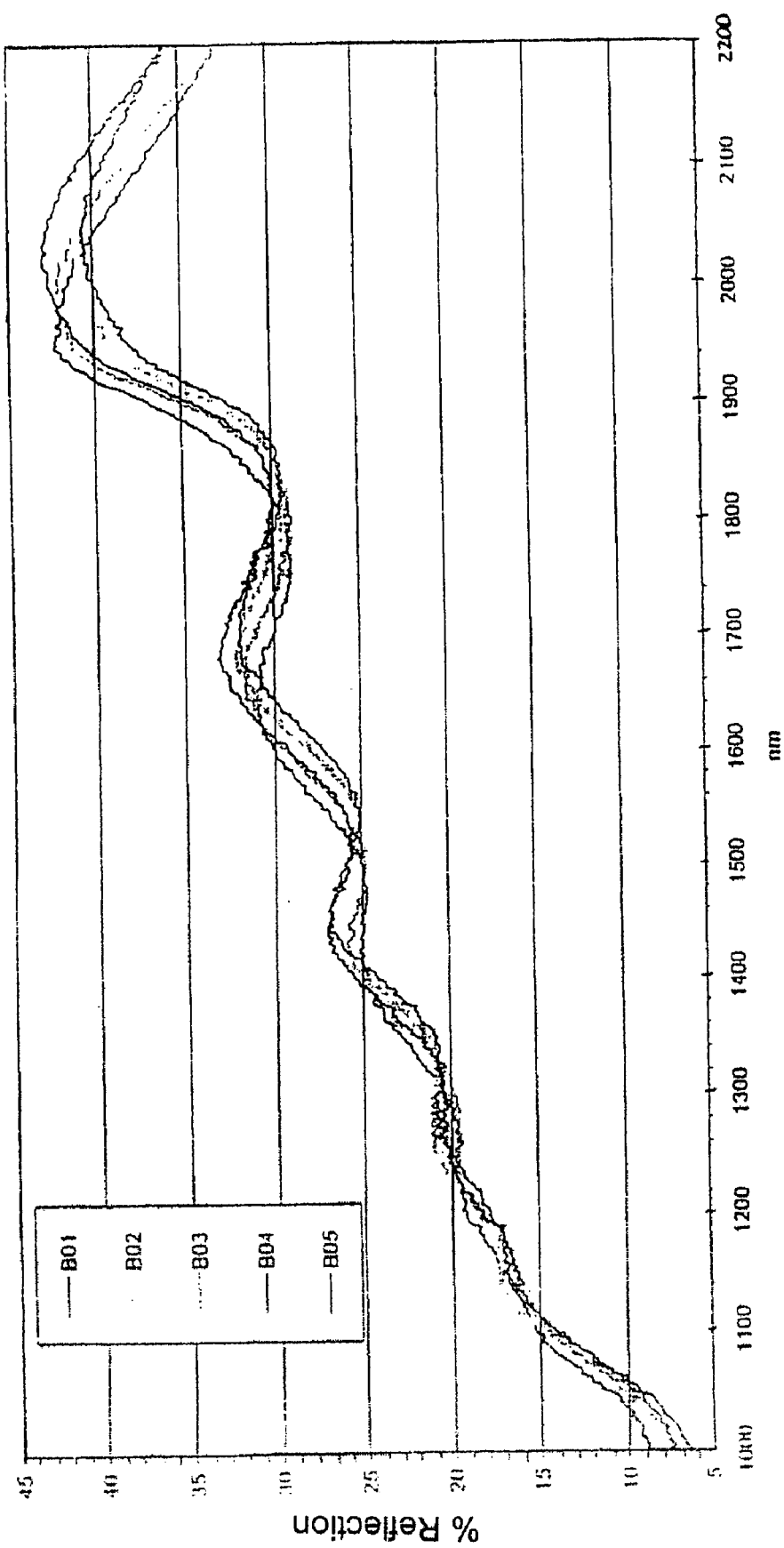
FIG. 6 shows reflection spectra in the NIR range in specimens with similar CIS layers.
Figure 7:
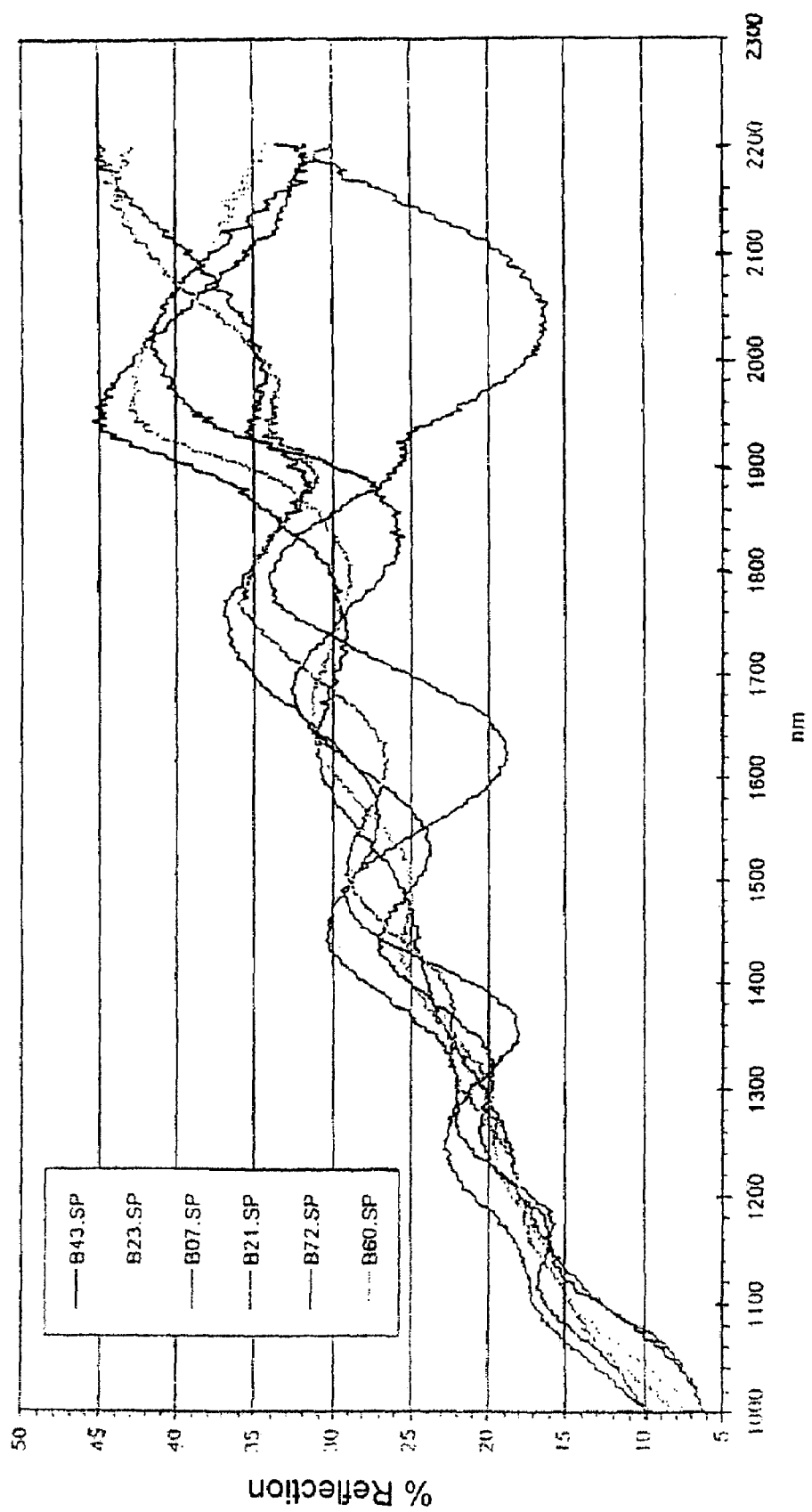
FIG. 7 shows reflection spectra in the NIR region in specimens with different CIS layers.

By way of example, FIG. 2 shows the curve shape of a measurement spectrum showing the reflectivity of a material layer as a function of wavelength.

This measurement spectrum is compared to a reference spectrum which is calibrated before the measurement has begun and which is stored in the signal processing device 10. Differences in relation to the reference spectrum are converted into corresponding correction signals by means of the signal processing device 10.

This measurement arrangement is suitable for carrying out the method steps according to the invention. It is possible, for example, to determine the characteristics of the layers in a layer system which is formed of a molybdenum layer, a CIS layer arranged above the latter, and a CdS layer arranged above the CIS layer. The thickness of the CdS layer is 20 nm to 90 nm, for example.

Like many other metals, molybdenum is partially transparent in various frequency ranges in the IR spectrum. With an incident measurement light angle of 45° and a detection angle of 45° (specular arrangement), for example, the layer thicknesses can be determined from the interference by the arrangement according to the invention. A measurement in the visible range is specifically suited to the measurement of roughness because particularly layers which are close to the surface can be detected due to opaqueness. By measuring the difference in spectral intensities in specular and diffuse arrangement, the roughness and its provenance can be determined based on the scatter effect.

The CIS layer is transparent in the near infrared region and the corresponding molybdenum layer located below the CIS layer is opaque in the NIR region. In this case, the arrangement according to the invention can be used in a particularly advantageous manner, since the layer thickness can be calculated very easily in a specular arrangement by way of the interference maxima and interference minima. The interference can also be determined in diffuse reflection; in addition, information about the chemical and morphological composition of the layer can also be obtained from the attenuation of the interference and the curve of the reflection.

The CIS layer is optically dense in the UV/VIA wavelength region, while the CdS layer can be measured in a definite manner even with this small thickness. The corresponding layer thicknesses can easily be calculated from the interference by making use of the linear relationship between the layer thickness and the position of the interference minima. The absorption of the semiconductor CdS is dominant in the UV region, and deductions can be made about the quality (including doping) of the layer and its semiconductor characteristics by way of the position and steepness of the absorption edge.

If required, a ZnO layer which may be applied in addition can also be assessed like the CdS layers.

The examples clearly show that multilayer systems can be qualified in a definite and sufficient manner also simultaneously by the selection, according to the invention, of the measurement areas and the combination of different measuring geometries.

Some measurement results which were obtained in connection with the determination of the thickness of the CdS layer are shown in FIGS. 3 to 7.

While the foregoing description and drawings represent the present invention, it will be obvious to those skilled in the art that various changes may be made therein without departing from the true spirit and scope of the present invention.

REFERENCE NUMBERS 1 measuring head
2 product
3 optical unit
4 illumination device
5 measurement surface
6 detector
7 Y-light guide
8 UV-VIS spectral photometer
9 NIR spectral photometer
10 signal processing
11 interface

The invention claimed is:

1. A method for determining geometric and optical characteristics of different layers of a layer system, comprising the steps of:
   predetermining the measuring apparatus and measurement methods for determining the characteristics of one of the respective layers depending on the optical characteristics of this layer and depending on the optical characteristics of layers situated above it in the measuring direction.

2. The method according to claim 1, wherein the determination of the characteristics of a plurality of layers of the layer system is carried out simultaneously, but with separate measuring apparatus and measuring methods for each layer depending on its optical characteristics and depending on the optical characteristics of the layers located above it.

3. The method according to claim 1, for a layer system comprising a molybdenum layer, a CIS layer arranged on the latter, and a CdS layer arranged above the CIS layer, wherein the spectral interference is measured in that IR radiation in a wavelength range for which the molybdenum layer is at least partially transparent is directed to the layer system and the layer thickness of the molybdenum layer is determined from the measurement results, the interference maxima and interference minima are measured in that NIR radiation in a wavelength range for which the CIS layer is at least partially transparent, but for which the molybdenum layer is not transparent, is directed to the layer system and the layer thickness of the CIS layer is determined from the measurement results, and the interference maxima and interference minima are measured in that UV or VIS radiation in a wavelength range for which the CdS layer is at least partially transparent, but for which the CIS layer is not transparent, is directed to the layer system and the layer thickness of the CdS layer is determined from the measurement results.

4. The method according to claim 3, wherein the spectral intensity is measured, in addition, with a specular and a diffuse arrangement and the roughness of the surface of the molybdenum layer is determined from the difference in the results based on the scattering effect.

5. The method according to claim 3, wherein the attenuation of the interference and/or the curve of the reflection of the NIR radiation are/is determined and information is obtained therefrom about the chemical and morphological makeup of the CIS layer.

6. The method according to claim 3, wherein the absorption of the UV and VIS radiation is determined and information about the quality of and semiconductor characteristics of the CdS layer is obtained from the position and steepness of the absorption edge.

7. A measuring device for determining geometric and/or optical characteristics of different layers of a layer system, comprising:
   at least one illumination device for illuminating a measurement surface on the product;
   at least one detector for the light coming from the measurement surface;
   a signal processing device which communicates with the signal outputs of the detector;
   said illumination device having radiation sources whose radiation completely covers the UV, VIS and IR wavelength regions; and
   detectors being provided for wavelength regions that directly adjoin one another;
   wherein the detectors and the signal processing device are constructed for evaluating in its entirety the light coming from the measurement surface with wavelengths of 200 nm to more than 2400 nm.

8. The measuring device according to claim 7, wherein a UV-VIS spectral photometer and an NIR spectral photometer are provided as detectors.

9. The measuring device according to claim 8, wherein the spectral photometers are constructed as diode array spectral photometers.

10. The measuring device according to claim 7, wherein the illumination device, the photometers and the signal processing device are integrated in a common measuring head which is positioned over the measurement surface, wherein the angle of incidence α of the radiation on the measurement surface is variable.

11. The measuring device according to claim 7, wherein the signal processing device has an interface for coupling to an external computer and/or for a display device.

12. The measuring device according to claim 7, wherein flexible light guides are provided for transmitting the light proceeding from the illumination device and directed to the measurement surface and for transmitting the light proceeding from the measurement surface to the photometers.

13. The measuring device according to claim 6, wherein the light guides comprise a plurality of light-conducting fibers.

* * * * *